March 10, 1959 A. H. V. BLOOM Plant Pat. 1,817
PHLOX PANICULATA
Filed March 21, 1958
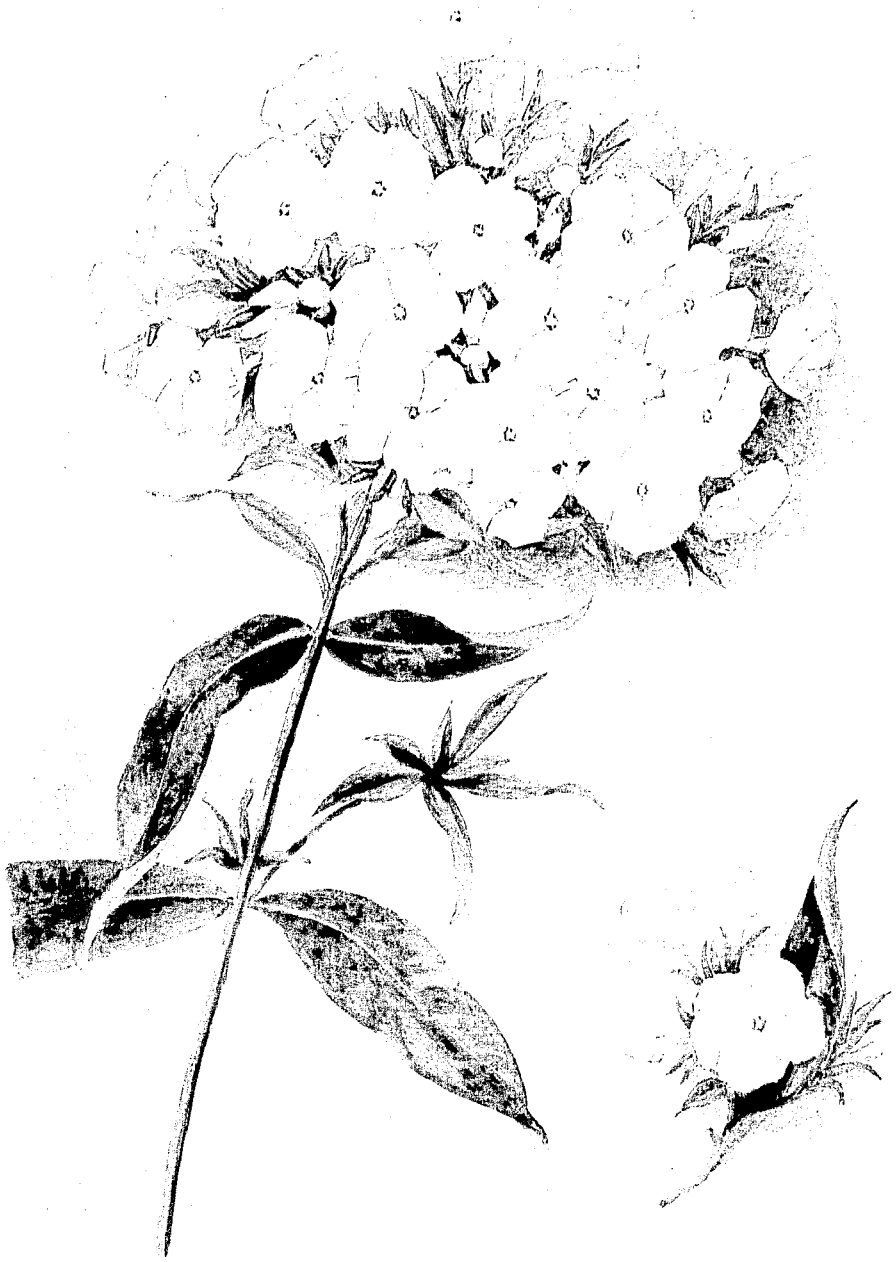
WITNESS
Addison E Avery
INVENTOR
Alan H. V. Bloom,
by:- John H Leonard,
his ATTY.

There are no petaloids in the center.

The aroma is faint, but otherwise usual for phlox blooms.

The genital organs do not appear to have any unusual characteristics.

The present variety of *Phlox paniculata* plant is characterized particularly in the pleasing flush of pink on the otherwise white petals, the firmness of the petals, and the unusual imbrication which gives an unusual resistance to adverse weather, the more than average vigorousness of growth and resultant adaptability to different locations and conditions of growth, and its strong stems.

Having shown and described my new variety of *Phlox paniculata* plant, and its manner of asexual reproduction, I claim:

The new and distinct variety of *Phlox paniculata* plant herein shown and described.

No references cited.